(12) United States Patent
Conrath et al.

(10) Patent No.: US 12,383,544 B2
(45) Date of Patent: Aug. 12, 2025

(54) METHODS FOR THE TREATMENT OF POLYCYSTIC KIDNEY DISEASE

(71) Applicant: Galapagos NV, Mechelen (BE)

(72) Inventors: Katja Els Conrath, Mechelen (BE); Reginald Christophe Xavier Brys, Mechelen (BE); Thierry Jean-Claude Marie Christophe, Mechelen (BE); Ronald Van Der Geest, Tilburg (NL)

(73) Assignee: Galapagos NV, Mechelen (BE)

( * ) Notice: Subject to any disclaimer, the term of this patent is extended or adjusted under 35 U.S.C. 154(b) by 850 days.

(21) Appl. No.: 17/605,623

(22) PCT Filed: Apr. 21, 2020

(86) PCT No.: PCT/EP2020/061083
§ 371 (c)(1),
(2) Date: Oct. 22, 2021

(87) PCT Pub. No.: WO2020/216740
PCT Pub. Date: Oct. 29, 2020

(65) Prior Publication Data
US 2022/0202802 A1    Jun. 30, 2022

(30) Foreign Application Priority Data
Apr. 24, 2019  (GB) ..................................... 1905711

(51) Int. Cl.
*A61K 31/4545* (2006.01)
*A61K 31/155* (2006.01)
(Continued)

(52) U.S. Cl.
CPC ........ *A61K 31/4545* (2013.01); *A61K 31/155* (2013.01); *A61K 31/55* (2013.01);
(Continued)

(58) Field of Classification Search
CPC .. A61K 31/4545; A61K 31/155; A61K 31/55; A61K 45/06; A61K 2300/00; A61P 13/12; C07D 487/04; C07D 471/04
See application file for complete search history.

(56) References Cited

U.S. PATENT DOCUMENTS

2009/0197911 A1    8/2009  Georg et al.

FOREIGN PATENT DOCUMENTS

WO    2011019737 A1    2/2011
WO    2013180310 A1    12/2013
(Continued)

OTHER PUBLICATIONS

Rysz et al., Combination drug versus monotherapy for the treatment of autosomal dominant polycystic kidney disease, Exp. Op. Pharmacother., 17, pp. 2049-2056 (Year: 2016).*
(Continued)

*Primary Examiner* — Jeffrey S Lundgren
*Assistant Examiner* — Alexander K. Showalter
(74) *Attorney, Agent, or Firm* — ArentFox Schiff LLP

(57) ABSTRACT

The present invention discloses compounds according to Formula I:
(Continued)

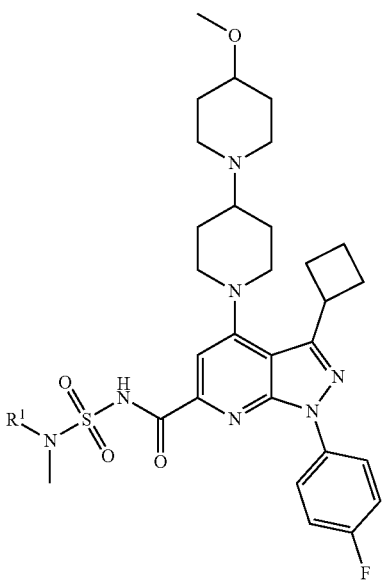

Wherein R¹ is as defined herein.

The present invention relates to compounds, methods for their production, pharmaceutical compositions comprising the same, and methods of treatment using the same, for the prophylaxis and/or treatment of that may be useful in the prophylaxis and/or treatment of polycystic kidney disease (PKD), by administering the compound of the invention.

16 Claims, 2 Drawing Sheets

(51) Int. Cl.
A61K 31/55 (2006.01)
A61K 45/06 (2006.01)
A61P 13/12 (2006.01)
C07D 487/04 (2006.01)

(52) U.S. Cl.
CPC .............. *A61K 45/06* (2013.01); *A61P 13/12* (2018.01); *C07D 487/04* (2013.01)

(56) References Cited

FOREIGN PATENT DOCUMENTS

| WO | 2016073470 A1 | 5/2016 | |
|---|---|---|---|
| WO | 2017/060879 A | 4/2017 | |
| WO | WO-2017060874 A1 * | 4/2017 | ........... A61K 31/437 |
| WO | 2018237174 A2 | 12/2018 | |

OTHER PUBLICATIONS

Yang et al., Small-Molecule CFTR Inhibitors Slow Cyst Growth in Polycystic Kidney Disease, J. Am. Soc. Nephrol., 19, pp. 1300-1310 (Year: 2008).*

Torres V.E. et al, "Autosomal dominant polycystic kidney disease", The Lancet, 2007, vol. 369, No. 9569, pp. 1287-1301.

Yang B. et al., "Small-Molecule CFTR Inhibitors Slow Cyst Growth in Polycystic Kidney Disease", J. Am. Soc. Nephrol. JASN, 2008, vol. 19, No. 7, pp. 1300-1310.

Torres V.E., "Treatment Strategies and Clinical Trial Design in ADPKD", Adv. Chronic Kidney Dis., 2010, vol. 17, No. 2, pp. 190-204.

Thiagarajah J.R. et al., "CFTR Inhibitors for Treating Diarrheal Disease", Clin. Pharmacol. Ther., 2012, vol. 92, No. 3, pp. 287-290.

Galietta L.V.J. et al., "Cell-based assay for high-throughput quantitative screening of CFTR chloride transport agonists", Am. J. Physiol.-Cell Physiol., 2001, vol. 281, No. 5, pp. C1734-C1742.

Fulcher M.L. et al., "Well-differentiated human airway epithelial cell cultures", Methods Mol. Med., 2005, vol. 107, pp. 183-206.

Booij T. H. et al., "High-Throughput Phenotypic Screening of Kinase Inhibitors to Identify Drug Targets for Polycystic Kidney Disease," SLAS Discov. Adv. Life Sci. RD, 2017, vol. 22, No. 8, pp. 974-984.

Lee, Edmund C. et al. 2019. "Discovery and Preclinical Evaluation of Anti-MIR-17 Oligonucleotide RGLS4326 for the Treatment of Polycystic Kidney Disease," Nature Communications 10 (1): 4148.

International Search Report and Written Opinion Issued on Jun. 10, 2020 in PCT/EP2020/061083.

* cited by examiner

METHODS FOR THE TREATMENT OF POLYCYSTIC KIDNEY DISEASE

CROSS-REFERENCE TO RELATED APPLICATIONS

This application is a National Stage Entry of PCT/EP2020/061083, filed Apr. 21, 2020, which claims priority to GB application No. 1905711.6, filed Apr. 24, 2019, the disclosures of each of which are hereby incorporated by reference in their entirety.

FIELD OF THE INVENTION

The present invention relates to compounds that may be useful in the prophylaxis and/or treatment of polycystic kidney disease (PKD). The present invention also provides methods for the production of the compound of the invention, pharmaceutical compositions comprising the compound of the invention, methods for the prophylaxis and/or treatment of polycystic kidney disease (PKD) by administering the compound of the invention.

BACKGROUND OF THE INVENTION

Polycystic kidney disease (PKD) is characterized by massive enlargement of fluid-filled cysts of renal tubular origin that compromise normal renal parenchyma and cause renal failure. Human autosomal dominant PKD (ADPKD), a prevalent form of PKD is caused by mutations in one of two genes, PKD1 and PKD2, encoding the interacting proteins polycystin-1 and polycystin-2, respectively, and is the most common of the inherited renal cystic diseases. (Torres, Harris, and Pirson 2007)

In PKD development, the total kidney volume increases exponentially creating cysts, whereas renal function decreases conversely, in particular the glomerular filtration rate (GFR). This leads progressively to aciduria, kidney stone formation, pain, blood pressure increase and finally death either through aneurysm, or cardiac insufficiency. (Torres, Harris, and Pirson 2007)

In addition, cysts may break leading to infections; usually difficult to treat and often requiring lengthy antibiotic treatments which may lead to antibiotic resistance.

Recently, it has been identified that the cyst development, may require chloride transport by the cystic fibrosis transmembrane conductance regulator (CFTR), wherein the CFTR could be responsible for generating and maintaining the fluid-filled cysts. (Yang et al. 2008) Therefore, inhibiting CFTR would prevent or reduce cysts formation and/or growth.

To date, there is no cure and only one Food and Drug Administration (FDA) approved treatment for PKD. Moreover, current treatment focus on managing disease complications due to the disease (Torres 2010), such as blood pressure lowering agents administration, and dialysis in the later stages of the disease; however, in the final stages kidney transplants remains the sole option. The prevalence of ADPKD is estimated to 1 in a 1000 individuals, with 600,000 people affected in the USA alone, where every year around 2144 patients start renal replacement therapy. (Torres, Harris, and Pirson 2007)

In addition, it has also been identified that CFTR inhibition could benefit patients with diarrheal disease as excessive fluid secretion in the intestine caused by enterotoxins results in activation of luminal Cl⁻ channels on enterocytes. (Thiagarajah and Verkman 2012)

Therefore the current therapies are not satisfactory, and there remains a need for new medicine for the prevention and/or treatment of PKD.

SUMMARY OF THE INVENTION

The present invention relates to compounds that may be useful in the prophylaxis and/or treatment of polycystic kidney disease (PKD), more particularly autosomal dominant polycystic kidney disease (ADPKD). The present invention also provides methods for the production of the compound of the invention, pharmaceutical compositions comprising the compound of the invention, methods for the prophylaxis and/or treatment of polycystic kidney disease (PKD) by administering the compound of the invention.

Accordingly, in a first aspect of the invention, the compound of the invention according to Formula (I) is provided for use in the prophylaxis and/or treatment of polycystic kidney disease:

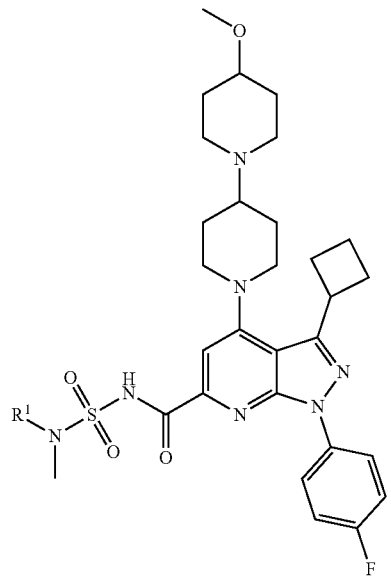

I wherein $R^1$ is H or —$CH_3$

In a more particular aspect, the compound of the invention are provided for use in the prophylaxis and/or treatment of polycystic kidney disease (PKD), and more particularly autosomal dominant polycystic kidney disease (ADPKD)

Surprisingly, whereas the compounds of the invention have CFTR modulatory activity in CF patients, in particular protein folding and trafficking activity (WO 2017/060874), it has been unexpectedly observed that they inhibit in wild type CFTR (non-CF diseased), and therefore may prevent and/or reduce cysts formation and/or growth, in particular in PKD, and/or ovarian cysts.

In a further aspect, the present invention provides pharmaceutical compositions for use in the prophylaxis and/or treatment of PKD, comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the treatment of PKD.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly PKD, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of PKD.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

DETAILED DESCRIPTION OF THE INVENTION

Definitions

Figure 1:
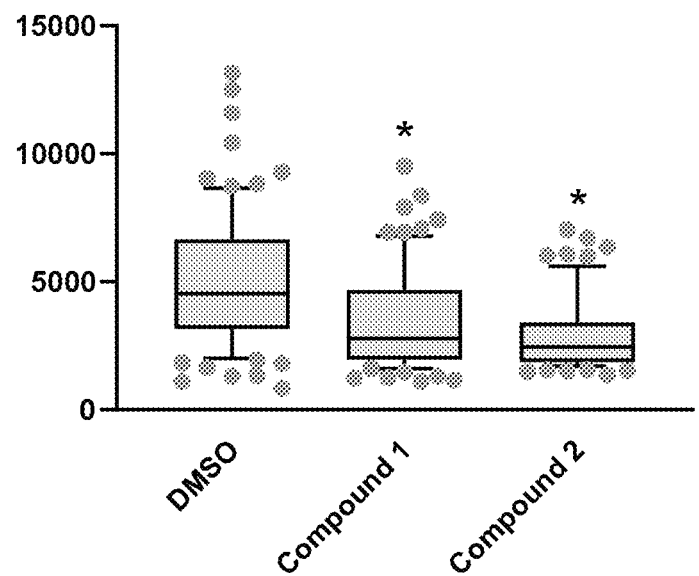
FIG. 1 shows the distribution of cyst sizes (cyst area, $\mu m^2$) in the 3D human cyst growth assay after 8 days of test compound Cpd 1 and Cpd 2 at 10 µM vs vehicle (DMSO) in box plot diagrams, wherein the box from bottom to top represents the 25% percentile value, the median value and the 75% percentile value of the data points, the bottom whisker represents the 10% percentile and the top whisker represents the 90% percentile.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzene sulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term 'metabolite' refers to compound(s) formed in a subject's body upon ingestion of the compound of the invention or pharmaceutical compositions thereof. Metabolites may further be metabolized, before being excreted from the body, for example, in the urine or bile. Metabolites may retain a similar or different pharmacological activity from the original drug and thereby contribute to the overall therapeutic activity of the compound of the invention. Metabolites may be formed through various reactions including oxidation (for example via cytochrome P450), reduction, hydrolysis, hydration, conjugation in liver microsomal enzyme system (for example with sulfate, glycine, and/or glucuronic acid), condensation and/or isomerisation.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term polycystic kidney disease (PKD) refers to the group of conditions in which the renal tubules become structurally abnormal, resulting in the development and growth of multiple cysts within the kidney. In particular, the term refers to autosomal dominant polycystic kidney disease (ADPKD) and autosomal recessive polycystic kidney disease (ARPKD). More particularly, the term refers to autosomal dominant polycystic kidney disease.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2$H or D), carbon-11 ($^{11}$C), carbon-13 ($^{13}$C), carbon-14 ($^{14}$C), nitrogen-13 ($^{13}$N), nitrogen-15 ($^{15}$N), oxygen-15 ($^{15}$O), oxygen-17 ($^{17}$O), oxygen-18 ($^{18}$O), phosphorus-32 ($^{32}$P), sulphur-35 ($^{35}$S), chlorine-36 ($^{36}$Cl), chlorine-37 ($^{37}$Cl), fluorine-18 ($^{18}$F) iodine-123 ($^{123}$I), iodine-125 ($^{125}$I) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Unnatural variant isotopic forms which incorporate deuterium i.e $^2$H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}$C, $^{18}$F, $^{15}$O and $^{13}$N, and would be useful in Positron Emission Topography (PET) studies for examining substrate receptor occupancy.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

THE INVENTION

The present invention relates to compounds that may be useful in the prophylaxis and/or treatment of polycystic kidney disease (PKD). The present invention also provides methods for the production of the compound of the invention, pharmaceutical compositions comprising the compound of the invention, methods for the prophylaxis and/or treatment of PKD by administering the compound of the invention.

Accordingly, in a first aspect of the invention, the compound of the invention according to Formula (I) is provided for use in the prophylaxis and/or treatment of PKD:

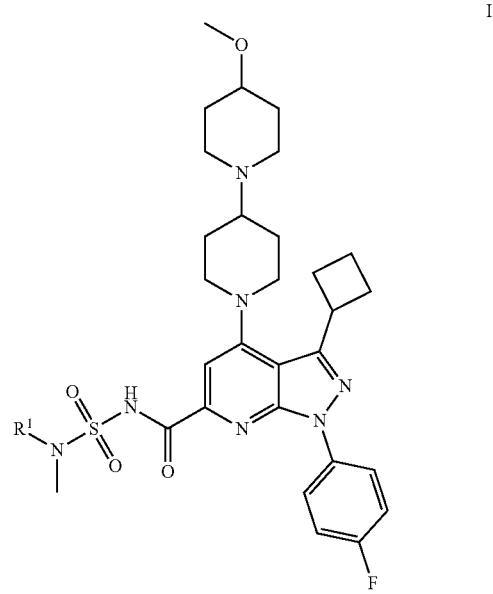

wherein $R^1$ is H or —CH$_3$.

In one embodiment, the compound of the invention is according to Formula I, wherein $R^1$ is H.

In one embodiment, the compound of the invention is according to Formula I, wherein $R^1$ is —CH$_3$.

In one embodiment, the compounds of the invention are provided in a natural isotopic form.

In one embodiment, the compounds of the invention are provided in an unnatural variant isotopic form. In a specific embodiment, the unnatural variant isotopic form is a form in which deuterium (i.e. $^2$H or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the illustrative example as examples.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

In a further aspect, the compound of the invention may be metabolized. In a particular aspect the metabolite of the compound of the invention may result from oxidation, reduction, hydrolysis, hydration, conjugation in liver microsomal enzyme system, condensation and/or isomerisation of a compound of the invention. In a particular aspect the metabolite of the compound of the invention may result from oxidation and conjugation with glucuronic acid of a compound of the invention. In a most particular aspect the metabolite is selected from M2, O-demethylated M2, M2 glucuronide, M3, Cpd 2 (M4), and O-demethylated M4:

M2

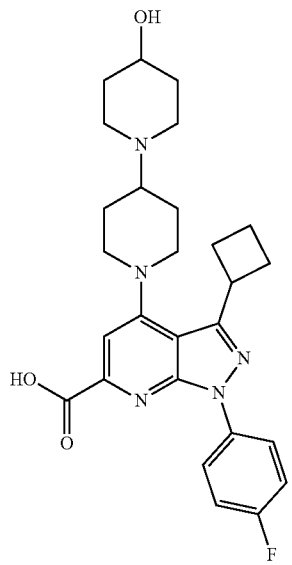

O-demethylaned M2

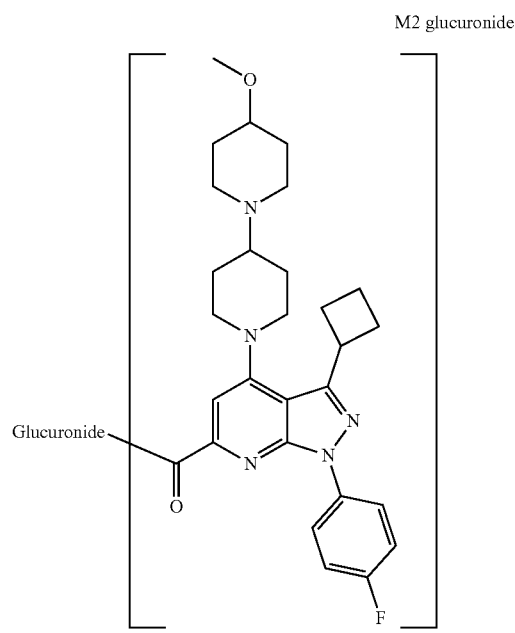

M2 glucuronide

M3

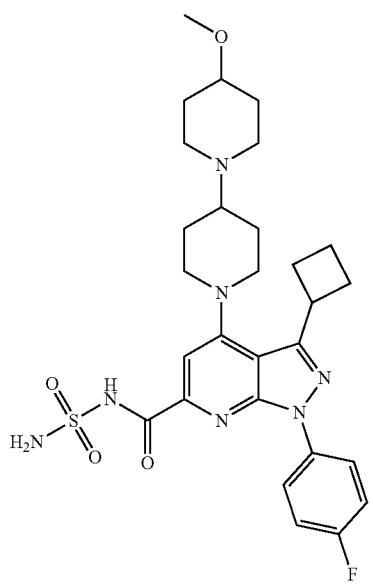

O-demethylated M4

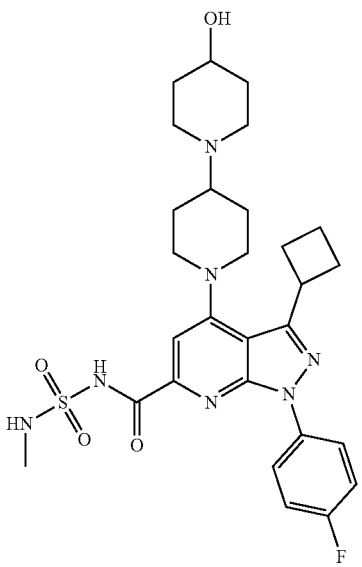

Cpd 2 (M4)

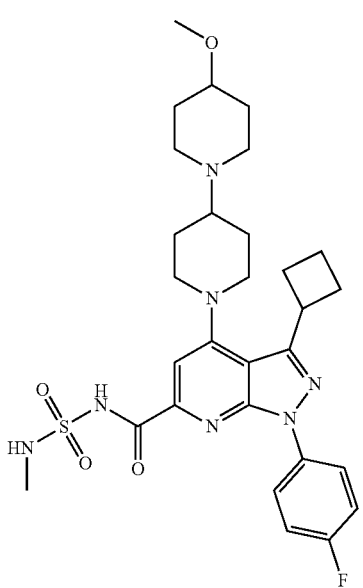

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism. (Bundgaard 1985) Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)

alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

PHARMACEUTICAL COMPOSITIONS

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, $17^{th}$ edition, 1985, Mack Publishing Company, Easton, Pennsylvania, which is incorporated herein by reference. (Remington and Gennaro 1985)

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

METHODS OF TREATMENT

In one embodiment, the present invention provides compounds of the invention, or pharmaceutical compositions comprising a compound of the invention for use in the prophylaxis and/or treatment of polycystic kidney disease (PKD). In in a particular embodiment, the PKD is autosomal dominant polycystic kidney disease (ADPKD).

In another embodiment, the present invention provides compounds of the invention, or pharmaceutical compositions comprising a compound of the invention for use in the manufacture of a medicament for use in the prophylaxis and/or treatment of PKD. In in a particular embodiment, the PKD is autosomal dominant polycystic kidney disease (ADPKD).

In additional method of treatment aspects, this invention provides methods of prophylaxis and/or treatment of a mammal afflicted with PKD, which methods comprise the administration of an effective amount of a compound of the invention or one or more of the pharmaceutical compositions herein described for the treatment or prophylaxis of said condition. In in a particular embodiment, the PKD is autosomal dominant polycystic kidney disease (ADPKD).

In one embodiment, the present invention provides pharmaceutical compositions comprising a compound of the invention, and another therapeutic agent. In a particular embodiment, the other therapeutic agent is a PKD treatment agent. In in a particular embodiment, the PKD is autosomal dominant polycystic kidney disease (ADPKD).

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving PKD, particular agents include, but are not limited to antagonist of vasopressin receptor, in particular antagonist of Vasopressin-2 receptor (tolvaptan, lixivaptan), pravastatin, venglustat, bosutinib, angiotensin-converting enzyme (ACE) inhibitors (e.g. benazepril, zofenopril, perindopril, trandolapril, captopril, enalapril, lisinopril, or ramipril), metformin, octapeptides (octreotide), cyclopeptides (lanreotide), short oligonucleotide inhibitor of microRNA (anti-miR) (e.g. anti-miR17 (RGLS4326) (Lee et al. 2019)) and angiotensin II receptor blockers (ARBs) (e.g. losartan, irbesartan, olmesartan, candesartan, valsartan, fimasartan and azilsartan). In a particular embodiment, the other therapeutic agent is selected from tolvaptan and metformin. In another particular embodiment, the other particular agent is RGLS4326.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

ABBREVIATIONS

| Abbreviation | Definition |
|---|---|
| ADPKD | autosomal dominant polycystic kidney disease |
| CAS# | Chemical American society number |
| CFTR | cystic fibrosis transmembrane conductance regulator |
| CF | cystic fibrosis |
| DBU | 1,8-Diazabicyclo[5.4.0]undec-7-ene CAS# 6674-22-2 |
| DMSO | dimethylsulfoxide |
| HEPES | 4-(2-hydroxyethyl)-1-piperazineethanesulfonic acid - CAS# 7365-45-9 |
| LCMS | Liquid chromatography coupled to mass spectrometry |
| LiHMDS | Lithium bis(trimethylsilyl) amide (CAS#4039-32-1) |
| MeCN | Acetonitrile |
| mg | milligram |
| equiv | equivalent |
| h | hour |
| equiv | equivalent |
| min | minutes |
| min | minutes |
| mL | milliliters |
| mmol | millimoles |
| μL | microliters |
| μm | micrometer |
| μm² | square micrometer |
| RT | Room temperature |
| N | Normal |
| g | gram |
| nM | nanomolar |
| PKD | polycystic kidney disease |
| wt CFTR | Wild type CFTR |
| TECC | Trans-epithelial clamp circuit |
| THF | Tetrahydrofuran |

CHEMICAL SYNTHETIC PROCEDURES

General

The compounds of the invention can be prepared as disclosed in WO 2017/060874.

In particular Cpd 1 is described in WO 2017/060874 on page 687 as Cpd 381, Cpd 2 (M4) is described in WO 2017/060874 on page 758 as Cpd 629, M3 is described in WO 2017/060874 on page 758 as Cpd 630, M2 is described in WO 2017/060873, on page 655 as Cpd 892; O-demethylated M2 is described in WO 2017/060873, on page 656 as Cpd 898

Example 1. Illustrative Synthesis

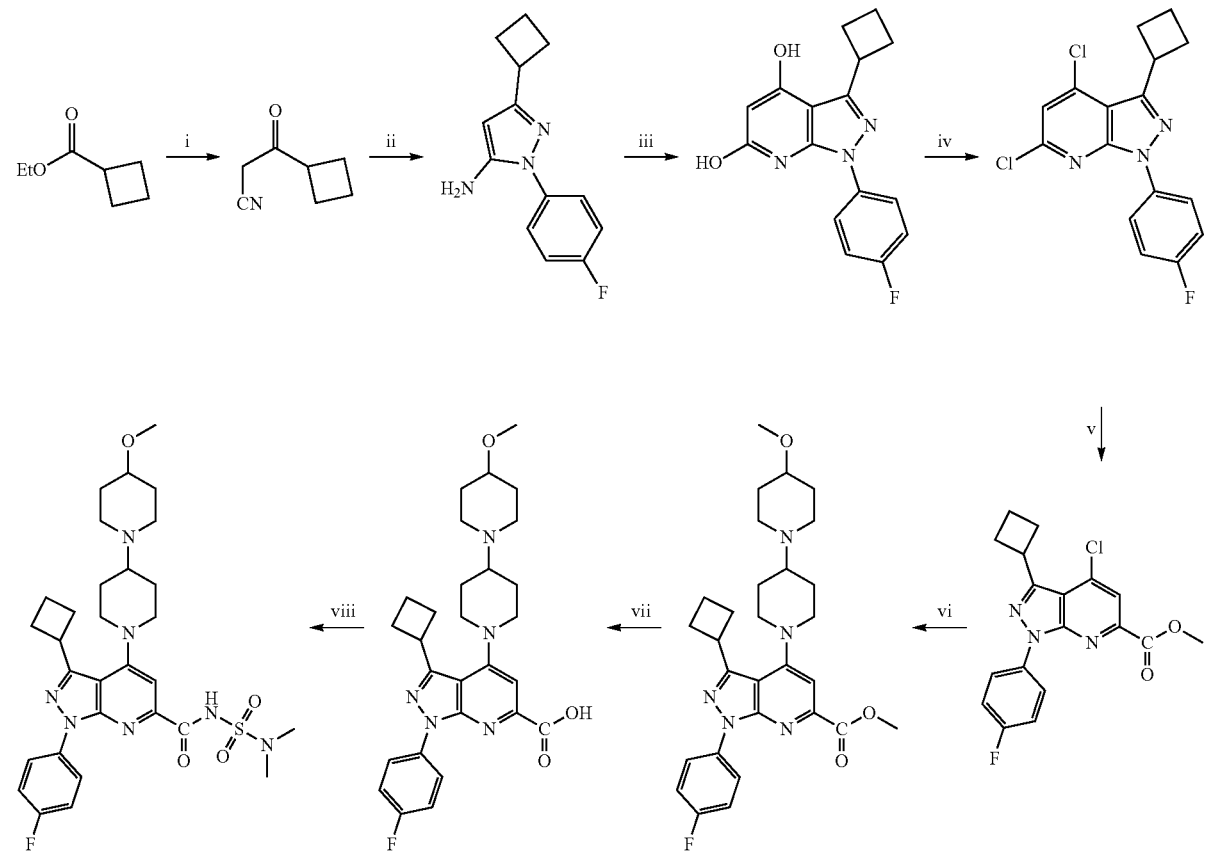

1.1. Step i: Cyclobutyl-3-oxo-propionitrile

A 1 L 4 neck round bottom flask was equipped with 2 dropping funnels and a septum on top of the apparatus. The whole system was flame-dried (heat gun) for 10 min under vacuum and then cooled down to RT under a positive stream of nitrogen (balloon). A low-temperature thermometer was adapted under a positive stream of nitrogen, then a 1 N LiHMDS solution in THF (468.0 mL, 468.0 mmol, 1.5 equiv) was cannulated into the flask using a positive stream of nitrogen. The solution was cooled down to −78° C. (dry ice/acetone cooling bath) as confirmed with the thermometer. Dry MeCN (24.4 mL, 468.0 mmol, 1.5 equiv) was added via syringe into the first dropping funnel, and then added dropwise (over 20 min) into the reaction mixture. After the end of the addition, the mixture was stirred at −78° C. for 1 h. At this point, cyclobutanecarboxylic acid ethyl ester (CAS #14924-53-9, 43.1 mL, 312.1 mmol, 1.0 equiv) as a solution in dry THF (106 mL) was introduced into the second dropping funnel. This solution was slowly added over 2 h into the reaction mixture at −78° C. The mixture was stirred at −78° C. for 2 h. The reaction mixture was poured into 300 mL of cold water, stirred for 30 min and allowed to warm to RT. The mixture was then partitioned between ethyl acetate and $H_2O$. The organic layer was separated, and the aqueous layer was extracted with ethyl acetate (3×300 mL). The combined organic phases were discarded. The aqueous layer was then acidified with 100 mL of 2 N HCl, then extracted with ethyl acetate (3×300 mL), washed with 50 mL of brine, dried over $MgSO_4$, filtered and concentrated in vacuo to afford the titled compound which was used without further purification.

1.2. Step ii: 3-cyclobutyl-1-(4-fluorophenyl)-1H-pyrazol-5-amine

A round bottom flask was charged with 3-cyclobutyl-3-oxo-propionitrile (10 g, 81.4 mmol), 4-fluorophenylhydrazine hydrochloride (CAS #823-85-8, 12 g, 74 mmol) and EtOH (35 mL). The reaction mixture was refluxed for 2 h and cooled down to RT. Half of the solvent was removed in vacuo. The mixture was vigorously stirred and diisopropyl ether (350 mL) was added. The stirring was continued for 1 h, and the formed precipitate was filtered, washed with diisopropyl ether and dried at 40° C. under reduced pressure to give the titled compound.

1.3. Step iii: 3-Cyclobutyl-1-(4-fluorophenyl)-1H-pyrazolo[3,4-b]pyridine-4,6-diol A mixture of 3-cyclobutyl-1-(4-fluorophenyl)-1H-pyrazol-5-amine (5 g, 18.6 mmol) and diethyl malonate (CAS #105-53-3, 8.5 mL, 55.8 mmol) was heated at 100° C. for 30 min and then at 170° C. for 3 h. The reaction mixture was cooled down to RT and dissolved in dichloromethane (60 mL). The resultant solution was poured into a stirred solution of n-heptane (700 mL). The precipitate was collected by filtration, washed with n-heptane and dried at 40° C. under reduced pressure to give the titled compound.

1.4. Step iv: 4,6-Dichloro-3-cyclobutyl-1-(4-fluorophenyl)-1H-pyrazolo[3,4-b]pyridine A three-neck round-bottom flask equipped with a Dean-Stark apparatus was charged with phenyl dichlorophosphate (CAS #770-12-7, 854 g, 4.05 mol). 3-Cyclobutyl-1-(4-fluorophenyl)-1H-pyrazolo[3,4-b]pyridine-4,6-diol (404 g, 1.35 mol) was added in portions over a period of 5 min. The temperature was increased to 170° C. over a period of 1 h, and the stirring at 170° C. was continued for 21 h. The reaction mixture was cooled down to 50° C. and added slowly to a stirred aqueous 4 N NaOH (5 L) keeping the temperature below 20° C. The suspension was stirred for 1 h at 10-15° C., and then cold water (3 L) was added. The precipitate was collected by filtration, washed with water and dried at 40° C. under reduced pressure to give the titled compound.

1.5. Step v: methyl 4-chloro-3-cyclobutyl-1-(4-fluorophenyl)-1H-pyrazolo[3,4-b]pyridine-6-carboxylate A pressured vessel was charged with 4,6-dichloro-3-cyclobutyl-1-(4-fluorophenyl)-1H-pyrazolo[3,4-b]pyridine (5 g, 14.9 mmol), Pd(dppf)Cl$_2$·DCM (CAS #95464-05-4, 218 mg, 0.3 mmol), and sodium acetate (1.8 g, 22.3 mmol) in dioxane/methanol (1:1, 25 mL). The system was loaded with CO (4 bars) and heated at 40° C. for 2 h. The vessel was cooled to RT, and the conversion was monitored by LCMS. The reaction vessel was charged again with CO (4 bars) and heated at 40° C. The sequence was repeated until full conversion was observed. The crude mixture was concentrated under reduced pressure and purified by flash column chromatography eluting with a mixture of nheptane/dichloromethane (90/10 to 30/70) to give the titled compound.

1.6. Step vi: methyl 3-cyclobutyl-1-(4-fluorophenyl)-4-[4-(4-methoxy-1-piperidyl)-1-piperidyl]pyrazolo[3,4-b]pyridine-6-carboxylate To a solution of methyl 4-chloro-3-cyclobutyl-1-(4-fluorophenyl)-1H-pyrazolo[3,4-b]pyridine-6-carboxylate (8.11 g, 22.6 mmol) in dry N-methylpyrrolidinone (100 mL) was added 4-methoxy-1,4'-bipiperidine (5.37 g, 27.1 mmol) and diisopropylethylamine (9.42 mL, 54.2 mmol). The reaction mixture was stirred at 100° C. for 24 h and then cooled down to ambient temperature and diluted with water. A suspension formed upon cooling at 0° C. The suspension was filtered, and the obtained precipitate was washed with water. After drying, the titled compound was obtained.

1.7. Step vii: 3-cyclobutyl-1-(4-fluorophenyl)-4-[4-(4-methoxy-1-piperidyl)-1-piperidyl]pyrazolo[3,4-b]pyridine-6-carboxylic Acid Methyl 3-cyclobutyl-1-(4-fluorophenyl)-4-[4-(4-methoxy-1-piperidyl)-1-piperidyl]pyrazolo[3,4-b]pyridine-6-carboxylate (80 μmol) was dissolved in a mixture of THF/ethanol (1/1; 6 mL) and 1 N sodium hydroxide (0.5 mL, 500 μmol) in water was added at RT. The solution was stirred for 4 h. Aqueous 1 N HCl (0.5 mL, 500 μmol) and a phosphate buffer were added (pH 6.2). The solvent was partially removed under reduced pressure, and the resulting mixture was extracted twice with chloroform. The combined organic phases were dried over magnesium sulfate, filtered and evaporated under reduced pressure to give the titled compound.

1.8. Step viii: N-(dimethylsulfamoyl)-1-(4-fluorophenyl)-4-[4-(4-methoxypiperidin-4-yl)piperidin-1-yl]-3-(propan-2-yl)-1H-pyrazolo[3,4-b]pyridine-6-carboxamide 3-cyclobutyl-1-(4-fluorophenyl)-4-[4-(4-methoxy-1-piperidyl)-1-piperidyl]pyrazolo[3,4-b]pyridine-6-carboxylic acid (0.15 mmol) and carbonyl diimidazole (37 mg, 0.23 mmol) were stirred in anhydrous DMF (800 μL) at room temperature for 1 h. Then for Cpd 1 N,N-dimethylsulfamide (37 mg, 0.30 mmol) or for Cpd 2 N-methylsulfamide (33 mg, 0.30 mmol) and triethylamine (42 μL, 0.30 mmol) were added, followed by slow addition of DBU (34 μL, 0.23 mmol). The reaction mixture was stirred 30 min at room temperature, diluted with methanol and purified by preparative HPLC on a Waters® Sunfire™ C8 column (30×150 mm) with a 40 to 70% gradient of acetonitrile in 10 mM aqueous ammonium acetate to give the titled compound.

Cpd 1 NMR (400 MHz, CDCl$_3$) δ ppm 8.01 ppm (dd, J=8.84, 4.55 Hz, 2H), 7.44 ppm (s, 1H), 7.25 ppm (t, J=8.46 Hz, 2H), 4.03-3.94 ppm (m, 1H), 3.73-3.69 ppm (m, 2H), 3.37 ppm (s, 3H), 3.3-3.24 ppm (m, 1H), 3.04 ppm (s, 6H), 2.97-2.87 ppm (m, 4H), 2.65-2.56 ppm (m, 2H), 2.52-2.36 ppm (m, 5H), 2.13-2.02 ppm (m, 4H), 1.9 ppm (s, 2H), 2.01-1.9 ppm (m, 2H), 1.73-1.61 ppm (m, 3H)

Cpd 2 NMR (400 MHz, CDCl$_3$) δ ppm 7.90-8.08 (m, 2H), 7.45 (s, 1H), 7.13-7.36 (m, 2H), 5.65 (d, J=4.6 Hz, 1H), 3.87-4.00 (m, 1H), 3.82 (d, J=12.2 Hz, 2H), 3.65 (br. s., 1H), 3.39 (s, 3H), 3.15-3.45 (m, 4H), 3.04 (t, J=12.0 Hz, 2H), 2.73-2.87 (m, 3H), 2.35-2.70 (m, 9H), 1.94-2.22 (m, 6H).

TABLE I

Illustrative compounds of the invention

| Cpd# | Name | MW | Mes |
|---|---|---|---|
| 1 | 3-cyclobutyl-1-(4-fluorophenyl)-4-(4-methoxy[1,4′-bipiperidin]-1′-yl)-N-(dimethylsulfamoyl)-1H-pyrazolo[3,4-b]pyridine-6-carboxamide | 613 | 614 |
| 2 | 3-cyclobutyl-1-(4-fluorophenyl)-4-(4-methoxy[1,4′-bipiperidin]-1′-yl)N-(methylsulfamoyl)-1H-pyrazolo[3,4-b]pyridine-6-carboxamide | 599 | 600 |

BIOLOGICAL EXAMPLES

Example 2. In Vitro Assays

2.1. Yellow Fluorescent Protein (YFP) Halide Assay in Wild Type CFTR 2.1.1. Assay Principle To evaluate the ability of a test compound to inhibit wild type CFTR, a YFP halide assay using HEK293 cells transfected with wild type human CFTR was developed. (Galietta, Jayaraman, and Verkman 2001) Cells were incubated during 24 h with a dose range of test compound and the resulting wild type CFTR activity was plotted to obtain the $EC_{50}$.

Test compounds were also added together with forskolin to wild type CFTR expressing cells in order to fully active the available CFTR at the plasma membrane and determine accurately the inhibition of the channel activity.

2.1.2. Protocol

HEK293 cells were transfected with 10 to 80 ng of wild type CFTR and 20 ng of plasmid encoding YFP (H148Q/I152L/F47L) using jetPEI (Polyplus transfection). Directly after transfection, cells were seeded in black 96-well plates coated with Poly-D-lysine at a density of 70,000 cells per well. The next day, cells were treated with corrector(s) for 24 h. After this incubation period, cells were washed twice with DPBS with $Ca^{2+}$ and $Mg^{2+}$. Subsequently, cells were treated with 10 μM forskolin and the desired concentration of potentiator in a volume of 40 μl and incubated at room temperature for 10 min, a time point optimized in previous experiments resulting in a good window (positive control/negative control >2) and signal to background ratio. YFP fluorescence was measured using an EnVision plate reader (PerkinElmer). The signal was recorded for 7 seconds, starting just before injection of 110 μL NaI buffer (137 mM NaI, 2.7 mM KI, 1.7 mM $KH_2PO_4$, 10.1 mM $Na_2HPO_4$, 5 mM D-glucose) into the well with a speed of 150 μl/s, resulting in a final volume of 150 μl. The excitation wavelength was 485 nm and the emission wavelength 530 nm.

Concentration-response experiments were fitted using a 4 parameter hill function of the form Response=Bottom+(Top−Bottom)/(1+($EC_{50}$/concentration)^HillSlope)) to determine $EC_{50}$ values.

2.1.3. Results

In this assay, Cpd 1 inhibits WT CFTR with an $EC_{50}$ of 728 nM and Cpd 2 inhibits wt CFTR with an $EC_{50}$ of 102 nM

Example 3. TECC Assay

3.1. Assay Principle

The TECC assay is used to evaluate compounds on normal primary bronchial epithelial cells (HBE cells), which are closer to physiological conditions

3.2. Human Bronchial Epithelial (HBE) Cell Culture

Bronchial epithelial cells isolated from transplanted lungs from normal (wt CFTR) were isolated from lungs obtained from donors undergoing a planned transplantation. These primary cells were cultured directly on type IV collagen-coated polycarbonate Transwell supports with a diameter of 6.5 mm and pore size of 0.4 μm (Costar, #3397) for 18 to 25 days in air liquid (ali) interface essentially as previously described for TECC. (Fulcher et al. 2005)

3.3. Protocol

Trans-epithelial clamp circuit (TECC) recordings were performed using the TECC instrument developed and sold by EP Design (Bertem, Belgium). During the recording, the epithelial cells were bathed in a NaCl-Ringer solution (120 mM NaCl, 20 mM HEPES, 1.2 mM $CaCl_2$, 1.2 mM $MgCl_2$, 0.8 mM $KH_2PO_4$, 0.8 mM $K_2HPO_4$, 5 mM glucose, pH 7.4) on both the basolateral (640 μl) and the apical side (160 μl) and kept at 37° C. Apical amiloride was used to inhibit the endogenous ENaC currents (100 μM) while forskolin (0.3 μM) was applied on both the apical and basolateral sides to stimulate CFTR. All triggers and compounds used during the experiment were first dissolved in DMSO to a 1000× concentrated solution, just prior to treatment a 10× stock was prepared in the NaCl-Ringer solution which was used for addition of the correct concentration of trigger and or compound during the experiment. Cells were treated with test compounds for 24 hours before recording and this treatment was repeated in the TECC buffer prior to the electrophysiological recording. Measurements were done during a 20-min timeframe with recordings every 2 min. The transepithelial potential (PD) and transepithelial resistance (Rt) were measured in an open circuit and transformed to Ieq using Ohm's law. The maximal increase in Ieq (Δ Ieq) was used as a measure for the increased CFTR activity.

3.3.1. Results

In this assay, incubation of normal HBE cells with a combination of Cpd 1 and Cpd 2 resulted in a reduction of current from 10.7 μA/cm² (DMSO control; vehicle) to 3.06 μA/cm² (72% reduction of channel activity) when using 0.3 μM forskolin to activate the CFTR channel.

Incubation of normal HBE cells with a combination of Cpd 1 and Cpd 2 resulted in a reduction of current from 4.09 μA/cm² (DMSO control; vehicle) to 0.8 μA/cm² (80% reduction of channel activity) when using 0.1 μM forskolin to activate the CFTR channel.

Incubation of normal HBE cells with Cpd 1 alone resulted in a reduction of current from 14.4 μA/cm² (DMSO control; vehicle) to 6.6 μA/cm² (54% reduction of channel activity) with a p$IC_{50}$ of 6.97 (resulting in an $IC_{50}$ value of 108 nM) when using 0.3 μM forskolin to activate the CFTR channel.

Incubation of normal HBE cells with Cpd 2 alone resulted in a reduction of current from 14.1 μA/cm² (DMSO control; vehicle) to 5.9 μA/cm² (58% reduction of channel activity)) with a p$IC_{50}$ of 7.50 (resulting in an $IC_{50}$ value of 32 nM) when using 0.3 μM forskolin to activate the CFTR channel.

Channel activity in absence of forskolin resulted in a current of 0.25 μA/cm².

Example 4. Combination of Metformin and Compound 1 on CFTR Activity in an YHA Assay

4.1. Assay Principle

To evaluate the ability of a test compound combination to inhibit wild type CFTR using tubular kidney cells, a YFP halide assay using mIMCD3_wt cells (ATCC® CRL-2123) transfected with wild type mouse CFTR was developed (Galietta, Jayaraman, and Verkman 2001). Cells were incubated during 24 h with a dose range of compound 1 or a combination of a dose range of compound 1 with increasing dose of Metformin Immediately before measurement, forskolin together with a dose range of compound 1 combined or not with increasing dose of Metformin was added the wild type CFTR expressing mIMCD3 cells in order to fully activate the available CFTR at the plasma membrane. Inhibition of the channel by test compounds was plotted to obtain $IC_{50}$s.

4.2. Assay Protocol

Mouse mIMCD3_wt cells were transfected with 20 ng of wild type CFTR and 80 ng of plasmid encoding YFP (H148Q/I152L/F47L) using jetPEI (Polyplus transfection). Directly after transfection, cells were seeded in black 96-well plates coated with Poly-D-lysine at a density of 40,000 cells per well. The next day, cells were treated with compounds for 24 h. After this incubation period, cells were washed twice with DPBS with $Ca^{2+}$ and $Mg^{2+}$. Subsequently, cells were treated with 10 µM forskolin and the desired concentrations of compounds in a volume of 40 µl and incubated at room temperature for 15 min, a time point optimized in previous experiments resulting in a good window (positive control/negative control>2) and signal to background ratio. YFP fluorescence was measured using an EnVision plate reader (PerkinElmer). The signal was recorded for 7 seconds, starting just before injection of 110 µL NaI buffer (137 mM NaI, 2.7 mM KI, 1.7 mM $KH_2PO_4$, 10.1 mM $Na_2HPO_4$, 5 mM D-glucose) into the well with a speed of 150 µl/s, resulting in a final volume of 150 µl. The excitation wavelength was 485 nm and the emission wavelength 530 nm.

Concentration-response experiments were fitted using a 4 parameter hill function of the form Response=Bottom+(Top−Bottom)/(1+($EC_{50}$/concentration)^HillSlope)) to determine $EC_{50}$ values.

4.3. Results

When subjected to the above assay, the following results were obtained.

TABLE II $IC_{50}$s in the mIMCD3_wt YHA assay in presence of increasing concentrations of Metformin and Cpd 1 at 30 µM

| [Cpd 1] (µM) | [Metformin] (µM) | $IC_{50}$ (µM) |
| --- | --- | --- |
| 30 | 0 | 3.12 |
| 30 | 20 | 3.67 |
| 30 | 40 | 2.32 |
| 30 | 80 | 3.79 |
| 30 | 160 | 2.91 |
| 30 | 310 | 1.91 |
| 30 | 630 | 1.77 |
| 30 | 1250 | 1.82 |
| 30 | 2500 | 0.83 |
| 30 | 5000 | 0.92 |

Compound 1 alone at 30 µM was able to inhibit mouse CFTR activity in mouse mIMCD3_wt cells with an $EC_{50}$ of 3.12 µM.

In combination with Metformin, compound 1 was shown to inhibit mouse CFTR channel in mouse mIMCD3 cells with increasing potency when increasing dose of Metformin were combined to compound 1. When 5 µM of Metformin was combined with compound 1, compound 1 inhibited mouse CFTR with an $IC_{50}$ of 0.92 µM. The shift in potency observed when Metformin is combined with compound 1 may indicate an additive and/or synergistic effect of metformin with compound 1 on the inhibition of mouse CFTR in this assay.

Example 5. Cellular Assays 5.1. 3D Mice Cyst Assay 5.1.1. Assay Principle

This assays uses PKD1−/− knocked-down medullary mouse duct cells which form small cysts. This cysts are then further stimulated with forskolin causing their expansion. Test compounds are then added with additional forskolin in order to evaluate their ability to counteract cysts formation. After 3 days, these cells are imaged, to measure in particular cyst size, cell number, nucleus shape, wall thickness.

5.1.2. Assay Protocol

The 3D cyst culture assay has been performed with Pkd1-KO mouse-inner medullary collecting duct cells (mIMRFNPKD 5E4) cells as described previously. (Booij et al. 2017) In short: mIMRFNPKD $5.10^4$ cells were mixed with Cyst-Gel (OcellO B. V., Oortweg 21, Leiden, 2333CH, Netherlands). 15 µL of cell-gel mix was pipetted to 384-well plates (Greiner µClear, Greiner Bio-One B.V.) using a CyBio Felix 96/60 robotic liquid dispenser (Analyik Jena A G). Gel-cell mix was plated at a final cell density of 2250 cells per well. After gel polymerization at 37° C. for 30 min, 33 µL culture medium was added to each well. Cells were grown in gel for 96 h, after which the cells were co-exposed with forskolin (Calbiochem) and the following molecules: Rapamycin (SelleckChem, S1039), Staurosporin (SelleckChem, 51421) were used as cyst inhibiting or toxic control respectively. Test compounds were tested in the 3D assay at the indicated final concentrations. After 72 h, cultures were fixed with 4% Formaldehyde (Sigma Aldrich) and simultaneously permeabilized with 0.2% Triton-X100 (Sigma Aldrich) and stained with 0.25 µM rhodamine-phalloidin (Sigma Aldrich) and 0.1% Hoechst 33258 (Sigma Aldrich) in 1×PBS (Sigma Aldrich) for 2 days at 4° C., protected from light. After fixation and staining, plates were washed with 1×PBS, after which plates were sealed with a Greiner SilverSeal (Greiner Bio-One B.V.) and stored at 4° C. prior to imaging Imaging was done using Molecular Devices ImageXpress Micro XLS (Molecular Devices) with a 4× NIKON objective. For each well 34 images in the Z-direction were made for both channels, capturing the whole z-plane in each image. Image analysis for actin and nuclei was performed using Ominer software (OcellO BV.).

5.1.3. Results

Incubation of Cpd 1 (10 µM) in the 3D cyst assay for 72 h resulted in a cyst swelling of 14.5% compared to vehicle (set at 100%), corresponding to a reduction of 85.5% in cyst swelling.

Incubation of Cpd 2 (10 µM) in the 3D cyst assay for 72 h resulted in a cyst swelling of −1.7% compared to vehicle (set at 100%), corresponding to a reduction of 100% in cyst swelling.

5.2. 3D Human Cyst Growth Assay 5.2.1. Assay Principle

This assay was performed at DiscoveryBioMed, Inc (400 Riverhills Business Park, Suite 435, Birmingham, AL 35242-8101, USA) using human cells derived from human ADPKD donor kidneys which form cysts in 3D in culture. In this assay design, cysts were allowed to form for 4 days before test compounds treatment (Cyst reduction design). No particular trigger were used to support the cyst formation. Test compounds were evaluated for their ability to prevent the growth of already formed cysts as well as the formation of novel cysts. After 8 days of test compounds treatment, these cells were imaged to measure in particular cell number, cysts number and cysts size.

5.2.2. Assay Protocol

The 3D human cystogenesis assay has been performed with cells collected from cysts originated from Discovery BioMed's Autosomal Dominant Polycystic Kidney Disease (ADPKD) donor 5 with a confirmed mutation in pkd1 gene.

A reduction assay paradigm was selected to test the ability of the test compounds to slow or stop cyst expansion once cysts have already begun to form in the gel. Compound 1 and 2 were tested at 8 different doses (3 nM, 10 nM, 30 nM, 100 nM, 300 nM, 1 µM, 3 µM, and 10 µM).

Donor 5 cells were seeded into a proprietary Discovery BioMed biogel on Day 0 at 5,500 cells per well and test compounds or vehicle were added onto cells on Days 5, 7, 9, and 11. Proprietary Discovery BioMed RenalCyte Media with 2.5% FBS was used throughout the study to maintain the cells. Importantly, no stimulus, such as forskolin or arginine-vasopressin, was added. Images were acquired on Day 4 (before drug treatment) and on Day 12 at the conclusion of the experiment with a Cytation 5 (BioTek) using a 4× magnification objective where 6 images were captured and stitched together to form a complete field of a single well in an entire 384-well plate. Fields were captured at multiple points throughout the gel and the entire stack was converted into a z-projection. Brightfield images were analyzed using a deep-learning algorithm trained to recognize cysts and to measure their number and size. On Day 13, after image acquisition, cell number was estimated by use of Promega 3D CellTiterGlo (CTG).

5.2.3. Results

Incubation with Cpd 1 at the dose of 10 µM resulted in a decrease of 31% of the quantified human cyst area ($p<0.05$ to DMSO control, significance determined by 1-way ANOVA followed by Kruskal-Wallis post-hoc analysis). (FIG. 1)

Incubation with Cpd 2 at the dose of 10 µM resulted in a decrease of 41% of the quantified human cysts area ($p<0.05$ to DMSO control, significance determined by 1-way ANOVA followed by Kruskal-Wallis post-hoc analysis). (FIG. 1)

Figure 2:
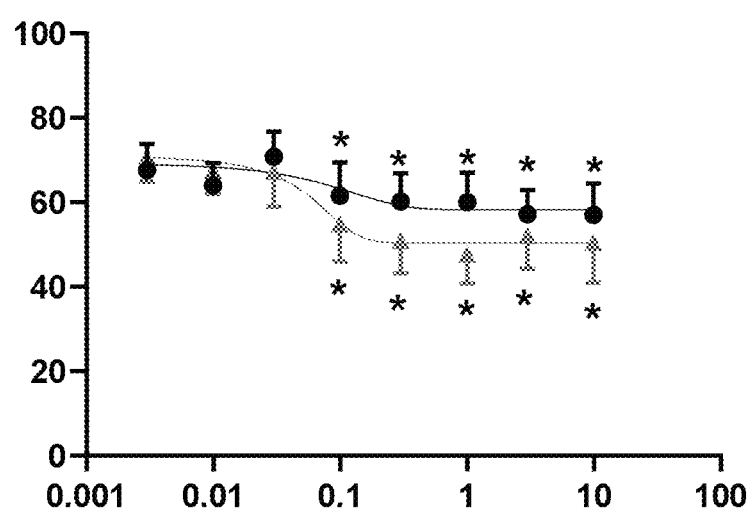
FIG. 2 shows the concentration dependent decrease in cyst numbers vs vehicle (DMSO) in the 3D human cyst growth assay after 8 days of test compound Cpd 1 filled circles) and Cpd 2 (filled triangle) at (3 nM, 10 nM, 30 nM, 100 nM, 300 nM, 1 µM, 3 µM, and 10 µM). The standard deviation is represented with bars for better visibility.

Incubation with Cpd 1 resulted in a concentration-dependent decrease in the number of human cysts formed. Cpd 1 showed significant effect from the dose of 0.1 µM up to the dose of 10 µM ($p<0.05$ to DMSO control, significance determined by 2-way ANOVA followed by Dunnett's post-hoc analysis). (FIG. 2)

Incubation with Cpd 2 resulted in a decrease in concentration-dependent decrease in the number of human cysts formed. Cpd 2 shown significant effect from the dose of 0.1 µM up to the dose of 10 µM ($p<0.05$ to DMSO control, significance determined by 2-way ANOVA followed by Dunnett's post-hoc analysis). (FIG. 2)

TABLE III

Box plot cyst size distribution for Cpd 1 & Cpd 2 vs vehicle (DMSO)

| Test Group | DMSO | Cpd 1 (10 µM) | Cpd 2 (10 µM) |
|---|---|---|---|
| Data points number | 85 | 71 | 67 |
| 10% Percentile (µm$^2$) | 1993 | 1608 | 1689 |
| 25% Percentile (µm$^2$) | 3141 | 1941 | 1858 |
| Median (µm$^2$) | 4526 | 2764 | 2444 |
| 75% Percentile (µm$^2$) | 6646 | 4682 | 3406 |
| 90% Percentile (µm$^2$) | 8647 | 6765 | 5589 |
| p value | NA | <0.0001 | <0.0001 |

TABLE IV

FIG. 2: Concentration dependent cyst size distribution for Cpd 1 and Cpd 2 vs vehicle (DMSO)

| Concentration (µM) | Cpd 1 | | | Cpd 2 | | |
|---|---|---|---|---|---|---|
| | Cyst n# | Standard deviation | p value | Cyst n# | Standard deviation | p value |
| 0 | 72 | 6.798693 | NA | 72 | 6.449806 | NA |
| 0.003 | 67.5 | 6.240548 | 0.6068 | 70.7 | 5.780846 | 0.9994 |
| 0.01 | 64 | 5.270463 | 0.077 | 67.5 | 5.400337 | 0.6068 |
| 0.03 | 70.7 | 5.945119 | 0.9994 | 67.2 | 8.419674 | 0.5366 |
| 0.1 | 61.5 | 7.835106 | 0.0084 | 54.9 | 9.81094 | <0.0001 |
| 0.3 | 60.2 | 6.646637 | 0.0021 | 50.9 | 7.947555 | <0.0001 |
| 1 | 60 | 6.960204 | 0.0017 | 47.8 | 7.308774 | <0.0001 |
| 3 | 57.1 | 5.743595 | <0.0001 | 52.1 | 7.955558 | <0.0001 |
| 10 | 57 | 7.363574 | <0.0001 | 50.5 | 9.137336 | <0.0001 |

TABLE V

Figure 3:
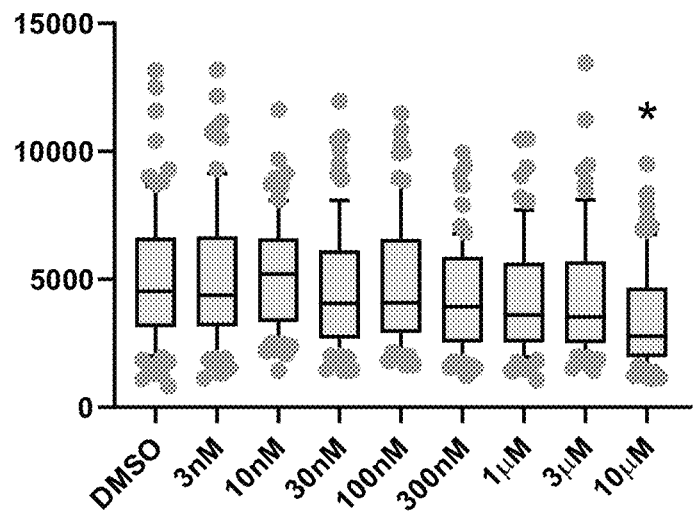
FIG. 3 shows the distribution of cyst sizes (cyst area, $\mu m^2$) vs vehicle (DMSO) in the 3D human cyst growth assay after 8 days of Cpd 1 at 3 nM, 10 nM, 30 nM, 100 nM, 300 nM, 1 µM, 3 µM, and 10 µM in box plot diagrams, wherein the box from bottom to top represents the 25% percentile value, the median value and the 75% percentile value of the data points, the bottom whisker represents the 10% percentile and the top whisker represents the 90% percentile.

FIG. 3 - Concentration dependent cyst size distribution for Cpd 1 vs vehicle (DMSO)

| Test Group | Data points number | 10% Percentile (µm$^2$) | 25% Percentile (µm$^2$) | Median (µm$^2$) | 75% Percentile (µm$^2$) | 90% Percentile (µm$^2$) | p value |
|---|---|---|---|---|---|---|---|
| DMSO | 85 | 1993 | 3141 | 4526 | 6646 | 8647 | NA |
| 3 nM | 77 | 2088 | 3172 | 4398 | 6698 | 9145 | >0.9999 |
| 10 nM | 71 | 2519 | 3346 | 5204 | 6607 | 8079 | >0.9999 |
| 30 nM | 78 | 2012 | 2670 | 4074 | 6130 | 8092 | >0.9999 |
| 100 nM | 71 | 2145 | 2897 | 4088 | 6588 | 8844 | >0.9999 |
| 300 nM | 71 | 1774 | 2517 | 3943 | 5897 | 6798 | >0.9999 |
| 1 µM | 69 | 1962 | 2530 | 3616 | 5655 | 7720 | 0.3339 |
| 3 µM | 65 | 2011 | 2500 | 3527 | 5710 | 8111 | 0.5649 |
| 10 µM | 71 | 1608 | 1941 | 2764 | 4682 | 6765 | <0.0001 |

TABLE VI

Figure 4:
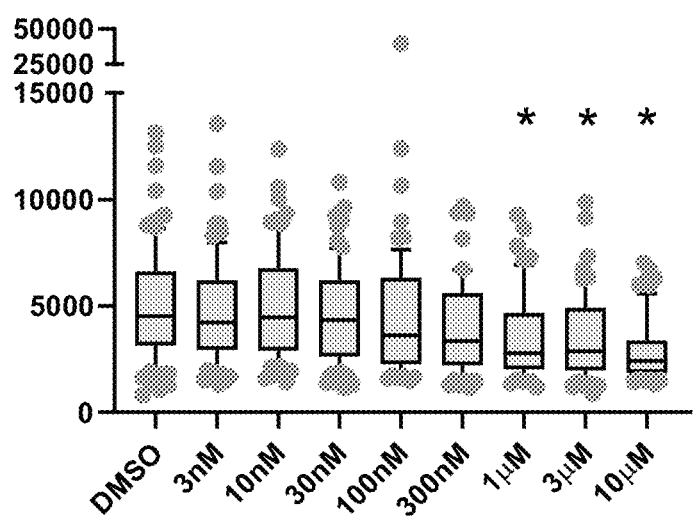
FIG. 4 shows the distribution of cyst sizes (cyst area, $\mu m^2$) vs vehicle (DMSO) in the 3D human cyst growth assay after 8 days of Cpd 2 at 3 nM, 10 nM, 30 nM, 100 nM, 300 nM, 1 µM, 3 µM, and 10 µM in box plot diagrams, wherein the box from bottom to top represents the 25% percentile value, the median value and the 75% percentile value of the data points, the bottom whisker represents the 10% percentile and the top whisker represents the 90% percentile.

| FIG. 4 - Concentration dependent cyst size distribution for Cpd 2 vs vehicle (DMSO) | | | | | | |
|---|---|---|---|---|---|---|
| Test Group | Data points number | 10% Percentile ($\mu m^2$) | 25% Percentile ($\mu m^2$) | Median ($\mu m^2$) | 75% Percentile ($\mu m^2$) | 90% Percentile ($\mu m^2$) | p value |

| Test Group | Data points number | 10% Percentile ($\mu m^2$) | 25% Percentile ($\mu m^2$) | Median ($\mu m^2$) | 75% Percentile ($\mu m^2$) | 90% Percentile ($\mu m^2$) | p value |
|---|---|---|---|---|---|---|---|
| DMSO | 85 | 1993 | 3141 | 4526 | 6646 | 8647 | NA |
| 3 nM | 84 | 1977 | 2946 | 4242 | 6213 | 7976 | >0.9999 |
| 10 nM | 77 | 2178 | 2918 | 4471 | 6789 | 8825 | >0.9999 |
| 30 nM | 81 | 1940 | 2641 | 4361 | 6223 | 7730 | >0.9999 |
| 100 nM | 66 | 1799 | 2294 | 3640 | 6330 | 7663 | 0.4492 |
| 300 nM | 65 | 1648 | 2218 | 3378 | 5611 | 6706 | 0.064 |
| 1 $\mu$M | 58 | 1615 | 2028 | 2787 | 4670 | 6944 | 0.0012 |
| 3 $\mu$M | 65 | 1493 | 1982 | 2894 | 4922 | 6220 | 0.0006 |
| 10 $\mu$M | 67 | 1689 | 1858 | 2444 | 3406 | 5589 | <0.0001 |

5.3. In Vivo Experiment in Combination with Tolvaptan

5.3.1. Model Principle

The ADPKD mice model is based on PKD1$^{flox/flox}$ (with lox sites flanking exons 2-4)/ubiquitous CreER$^{T2}$ mice in which the PKD1 gene is ubiquitously knock-out by the activation of the Cre recombinase by treatment of the mice with Tamoxifen at day 12 after birth (in nursing female). Homozygous knock-out of the PKD1 gene leads to the rapid formation of kidney cysts mimicking to a certain extend the development of ADPKD disease in human.

Test compounds (tolvaptan, Cpd 2 and a combination of tolvaptan+Cpd 2) were evaluated in this model for their ability to reduce the formation of kidney cysts (Cyst volume %) as well as their ability to protect mice kidney from failure, measured by the blood urea nitrogen (BUN) concentration, a marker of the kidney function.

In particular, urea nitrogen is a normal waste product in blood arising from the breakdown of food proteins and from body metabolism, which is normally removed by the kidneys. When kidney function slows down, the BUN level rises.

5.3.2. Assay Protocol

Before experimentations, mouse colonies of PKD1$^{flox/flox}$ (with lox sites flanking exons 2-4)/ubiquitous CreER$^{T2}$ were maintained at Charles River Laboratories (France). To induce Cre recombinase activity, tamoxifen (60 mg/kg in sunflower oil) was delivered in nursing females by intraperitoneal injection at postnatal day 12. Subsequently, tamoxifen-containing milk was administered to pups. Treatments started at 4 weeks of age for 11 weeks. Tolvaptan was incorporated in diet (0.1%) and given alone or in combination with Cpd 2, administered at 250 mg/kg, q. d., p.o. At initiation of treatment and on a regular basis during the study, serum was collected to determine levels of blood urea nitrogen (BUN) on a Spotchem bioanalyzer. At necropsy, kidneys were collected and weighed to determine kidney weight/body weight ratio.

For each mouse half of kidney cut in the sagittal plane were fixed for 24 h in Buffered formaldehyde (VWR, France) before paraffin embedding using standard procedure. Kidney sections were stained with hematoxylin prior to image analysis.

Cyst percentage was calculated from hematoxylin stained kidney section using Calopix™ image analysis software (Tribvn, France). Cystic percentage was measured as a ratio of cystic area to a total section area (Rodger et al, 2016). To estimate cyst volume, cyst percentage was multiplied by total 2 kidneys weight to determine total cyst weight, which was then converted to total cyst volume by assuming 1 g/mL of cyst fluid (Rodger et al, 2016).

Two independent experiments were conducted. A meta-analysis combining the results of the two experiments (BUN and cyst volume %) was conducted in order to increase ability to significantly determine the effect of Cpd 2 and its combination with tolvaptan.

5.3.3. Results of the Meta-Analysis

A two-way ANOVA with Dunnett post-hoc multiple comparisons of all experimental groups versus the diseased group has been applied to the log Fold Change (log FC) of BUN (mg/mL) at sacrifice (Week 15) versus BUN at Week 4 as function of Group and Study.

The mean fold change at week 15 (sacrifice) vs week 4 (treatment initiation) is calculated, assuming a 100% change for the diseased group (untreated).

TABLE VII

| BUN Mean fold changes on week 15 compared to week 4 in the study | | | |
|---|---|---|---|
| Group | Mean fold changes on week 15 vs week 4 | % of Mean Diseased fold change | adjusted p-value |
| Diseased | 2.341 | 100 | NA |
| Cpd 2 | 1.941 | 82.9 | 0.2068 |
| Tolvaptan | 1.889 | 80.7 | 0.0891 |
| Tolvaptan + Cpd 2 | 1.419 | 60.6 | <0.0001 |

Although administering tolvaptan or Cpd 2 alone from week 4 to week 15 did not result in a significant fold change vs the diseased group, the combination of tolvaptan and Cpd 2 results in statistically significant fold change difference compared to diseased group, indicating that tolvaptan in combination with Cpd 2 at the tested doses may affect disease progression.

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Booij, Tijmen H., Hester Bange, Wouter N. Leonhard, Kuan Yan, Michiel Fokkelman, Steven J. Kunnen, Johannes G. Dauwerse, et al. 2017. "High-Throughput Phenotypic Screening of Kinase Inhibitors to Identify Drug Targets for Polycystic Kidney Disease." *SLAS DISCOVERY: Advancing Life Sciences R&D* 22 (8): 974-84. https://doi.org/10.1177/2472555217716056.

Bundgaard, Hans. 1985. *Design of Prodrugs*. Elsevier.

Fulcher, M. Leslie, Sherif Gabriel, Kimberlie A. Burns, James R. Yankaskas, and Scott H. Randell. 2005. "Well-Differentiated Human Airway Epithelial Cell Cultures." *Methods in Molecular Medicine* 107: 183-206.

Galietta, Luis V. J., Sujatha Jayaraman, and A. S. Verkman. 2001. "Cell-Based Assay for High-Throughput Quantitative Screening of CFTR Chloride Transport Agonists." *American Journal of Physiology-Cell Physiology* 281 (5): C1734-42. https://doi.org/10.1152/ajpcell.2001.281.5.C1734.

Lee, Edmund C., Tania Valencia, Charles Allerson, Annelie Schairer, Andrea Flaten, Matanel Yheskel, Kara Kersjes, et al. 2019. "Discovery and Preclinical Evaluation of Anti-MiR-17 Oligonucleotide RGLS4326 for the Treatment of Polycystic Kidney Disease." *Nature Communications* 10 (1): 4148. https://doi.org/10.1038/s41467-019-11918-y.

Remington, Joseph P., and Alfonso R. Gennaro, eds. 1985. *Remington's Pharmaceutical Sciences*. 17 ed. Easton, Pa: Mack.

Thiagarajah, J R, and A S Verkman. 2012. "CFTR Inhibitors for Treating Diarrheal Disease." *Clinical Pharmacology & Therapeutics* 92 (3): 287-90. https://doi.org/10.1038/clpt.2012.114.

Torres, Vicente E. 2010. "Treatment Strategies and Clinical Trial Design in ADPKD."*Advances in Chronic Kidney Disease* 17 (2): 190-204. https://doi.org/10.1053/j.ackd.2010.01.006.

Torres, Vicente E, Peter C Harris, and Yves Pirson. 2007. "Autosomal Dominant Polycystic Kidney Disease." *The Lancet* 369 (9569): 1287-1301. https://doi.org/10.1016/S0140-6736(07)60601-1.

Yang, Baoxue, Nitin D. Sonawane, Dan Zhao, Stefan Somlo, and A. S. Verkman. 2008. "Small-Molecule CFTR Inhibitors Slow Cyst Growth in Polycystic Kidney Disease."

*Journal of the American Society of Nephrology: JASN* 19 (7): 1300-1310. https://doi.org/10.1681/ASN.2007070828.

The invention claimed is:

1. A method of prophylaxis and/or treatment of a mammal afflicted with polycystic kidney disease, comprising administering an effective amount of a compound according to Formula (I):

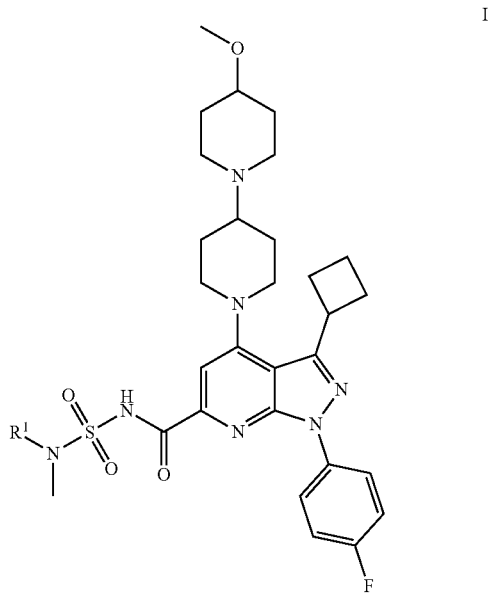

wherein $R^1$ is H or —$CH_3$;

or a pharmaceutically acceptable salt, or a solvate or the pharmaceutically acceptable salt of a solvate thereof, to the mammal.

2. The method according to claim 1, wherein $R^1$ is H.

3. The method according to claim 1, wherein $R^1$ is —$CH_3$.

4. The method according to claim 1, wherein the polycystic kidney disease is autosomal dominant polycystic kidney disease.

5. A method of prophylaxis and/or treatment of a mammal afflicted with polycystic kidney disease, comprising administering a pharmaceutical composition comprising a compound or pharmaceutically acceptable salt according to claim 1, and a pharmaceutically acceptable carrier, to the mammal.

6. The method according to claim 5, comprising administering a further therapeutic agent to the mammal.

7. The method according to claim 6, wherein the further therapeutic agent is a polycystic kidney disease treatment agent.

8. The method according to claim 6, wherein the further therapeutic agent is tolvaptan.

9. The method according to claim 6, wherein the further therapeutic agent is Metformin.

10. The method according to claim 5, wherein the polycystic kidney disease is autosomal dominant kidney disease.

11. The method according to claim 5, wherein $R^1$ is H.

12. The method according to claim 5, wherein $R^1$ is —$CH_3$.

13. The method according to claim 1, comprising administering a further therapeutic agent to the mammal.

14. The method according to claim 13, wherein the further therapeutic agent is a polycystic kidney disease treatment agent.

15. The method according to claim 13, wherein the further therapeutic agent is tolvaptan.

16. The method according to claim 13, wherein the further therapeutic agent is Metformin.

* * * * *